United States Patent [19]
Ouchi et al.

[11] Patent Number: 6,013,086
[45] Date of Patent: Jan. 11, 2000

[54] WIRE LOOP TYPE INSTRUMENT FOR ENDOSCOPE

[75] Inventors: Teruo Ouchi, Saitama; Miyuki Nishimura, Nagano, both of Japan

[73] Assignee: Asahi Kogaku Kogyo Kabushiki Kaisha, Tokyo, Japan

[21] Appl. No.: 09/126,771

[22] Filed: Jul. 31, 1998

[30] Foreign Application Priority Data

Aug. 28, 1997 [JP] Japan .................................. 9-231892

[51] Int. Cl.⁷ ............................ A61B 17/32; A61B 17/22
[52] U.S. Cl. ............................................ 606/113; 606/127
[58] Field of Search ................................... 606/110, 113, 606/127

[56] References Cited

U.S. PATENT DOCUMENTS 2,943,626  7/1960  Dormia .................................. 606/127
4,347,846  9/1982  Dormia .

FOREIGN PATENT DOCUMENTS 53-14060  4/1978  Japan .

Primary Examiner—Gene Mancene
Assistant Examiner—Michael B. Priddy
Attorney, Agent, or Firm—Greenblum & Bernstein, P.L.C.

[57] ABSTRACT

A wire loop type instrument for an endoscope having a plurality of elastic wires bundled together at distal and proximal ends thereof and adapted to form a loop shape as a whole. When withdrawn into the distal end of a sheath, the elastic wires are folded. When projecting from the distal end of the sheath, the elastic wires expand in the loop shape by their own elasticity. The elastic wires are inserted in a bundle into a pipe-shaped member at at least one of the distal and proximal ends thereof. The elastic wires are fixed to the pipe-shaped member by a fixing material such that portions of the elastic wires which are in the vicinity of the entrance of the pipe-shaped member are not fixed, but the elastic wires are fixed to the pipe-shaped member at portions thereof which are on the inner side of the vicinity of the entrance.

8 Claims, 5 Drawing Sheets (1)

(2)

(3)

(4)

WIRE LOOP TYPE INSTRUMENT FOR ENDOSCOPE

BACKGROUND OF THE INVENTION

The present disclosure relates to subject matter contained in Japanese Patent Application No. 9-231892 (filed on Aug. 28, 1997), which is expressly incorporated herein by reference in its entirety.

1. Field of the Invention

The present invention relates to a wire loop type instrument for an endoscope that has a wire loop at an end thereof.

2. Description of the Prior Art

Wire loop type instruments for endoscopes, such as a high-frequency snare and a basket type grasping instrument, have elastic wires expanded in a loop shape under free conditions. When withdrawn into the distal end of a sheath, the elastic wires are folded. When projecting from the distal end of the sheath, the elastic wires expand in the loop shape by their own elasticity.

Such a wire loop type instrument for an endoscope is generally arranged as shown in FIG. 9. A plurality of elastic wires 1 are bundled together at both the distal and proximal ends and inserted into binding pipes 2 and 5, respectively, in which the elastic wires 1 are fixed together.

A control wire 6 is axially movably inserted in a sheath 7. The distal end of the control wire 6 is firmly connected to the proximal end binding pipe 5, which fixedly binds together the proximal ends of the elastic wires 1.

In actual use of such a wire loop type instrument for an endoscope, the elastic wires 1 are axially moved back and forth to catch a polyp or other similar projection of tissue, and the polyp or the like caught in the loop is pinched tight with the elastic wires 1. Accordingly, the elastic wires 1 are repeatedly bent with a small radius of curvature at entrances A and B of the binding pipes 2 and 5 at the distal and proximal ends of the elastic wires 1.

Thus, the elastic wires 1 are inserted and fixed at both ends thereof in the respective binding pipes 2 and 5 and repeatedly bent at the borders between the fixed portions and the non-fixed portions thereof. Consequently, large stress concentration occurs at the bent portions of the elastic wires 1. Therefore, the elastic wires 1 are likely to break within a short period of time and readily develop a habit of bending undesirably.

SUMMARY OF THE INVENTION

An object of the present invention is to provide a durable wire loop type instrument for an endoscope in which elastic wires are unlikely to break at the bound portions thereof or to develop a habit of undesirably bending at the bound portions.

Other objects and advantages of the present invention will become apparent from the following detailed description of illustrated embodiments of the invention.

According to the present invention, there is provided a wire loop type instrument for an endoscope which has a plurality of elastic wires bundled together at distal and proximal ends thereof and adapted to form a loop shape as a whole. The elastic wires are capable of projecting from and withdrawing into the distal end of a sheath. When withdrawn into the distal end of the sheath, the elastic wires are folded. When projecting from the distal end of the sheath, the elastic wires expand in the loop shape by their own elasticity. The wire loop type instrument includes a pipe-shaped member having the elastic wires inserted therein in a bundle at at least one of the distal and proximal ends of the elastic wires. The elastic wires are fixed to the pipe-shaped member by a fixing material such that portions of the elastic wires which are in the vicinity of the entrance of the pipe-shaped member are not fixed, but the elastic wires are fixed to the pipe-shaped member at portions thereof which are on the inner side of the vicinity of the entrance.

BRIEF DESCRIPTION OF THE DRAWINGS

The present invention may be more fully understood from the description of preferred embodiments of the invention set forth below, together with the accompanying drawings, in which.

DESCRIPTION OF THE EMBODIMENTS

Embodiments of the present invention will be described below with reference to the accompanying drawings.

Figure 1:
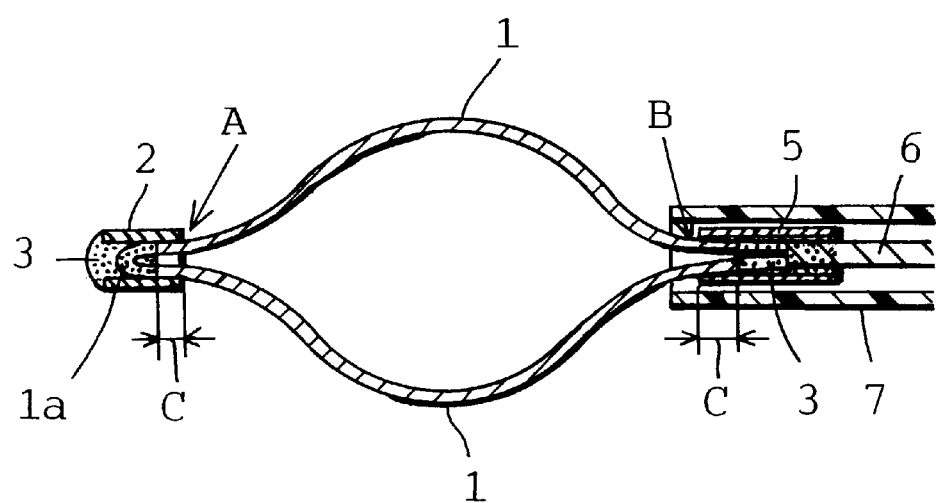
FIG. 1 is a sectional side view showing a distal end portion of a first embodiment of the present invention.

FIG. 1 shows a distal end portion of a high-frequency snare for an endoscope to which the present invention is applied. A single stock wire is bent through 180 degrees into a U-shape to form a bent portion 1a at a distal end thereof. A pair of elastic wires 1 extending from the bent portion 1a are smoothly curved to form a single loop as a whole. As the elastic wires 1, a stranded wire is used which is formed by twisting together a plurality of strands of stainless steel, for example.

At the bent portion 1a, the elastic wires 1 are bundled together and inserted into a distal end binding pipe 2, which is a short pipe of stainless steel, for example. The elastic wires 1 are fixed in the distal end binding pipe 2 by using a fixing material, e.g. a silver brazing material or a soldering material.

It should, however, be noted that the elastic wires 1 are not entirely fixed by the fixing material 3 in the distal end binding pipe 2. More specifically, the elastic wires 1 are not fixed at portions C which are in the vicinity of the entrance of the distal end binding pipe 2, but fixed by the fixing material 3 at portions thereof which are on the inner side (i.e. forward) of the portions C.

Figure 2:
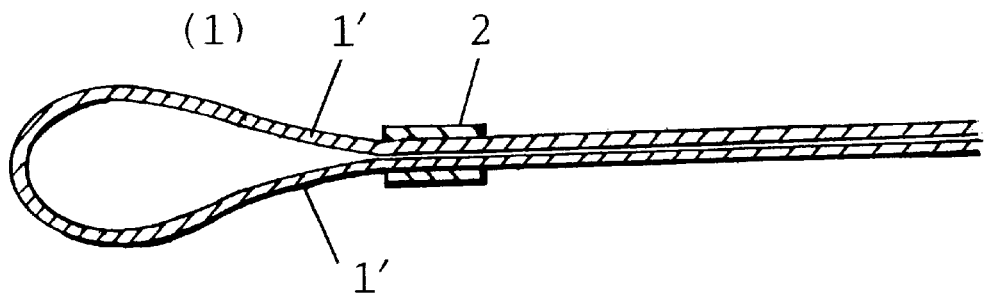
FIG. 2 shows a sequence of steps of processing a distal end bound portion of elastic wires according to the first embodiment of the present invention.
Figure 2:
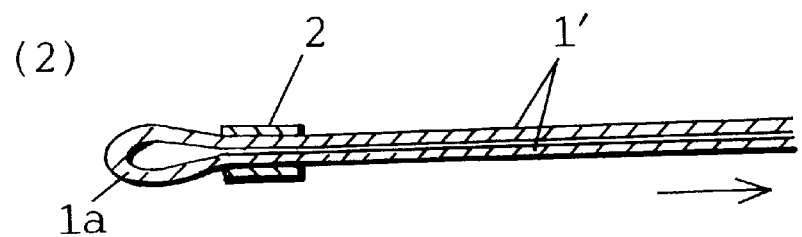
Figure 2:
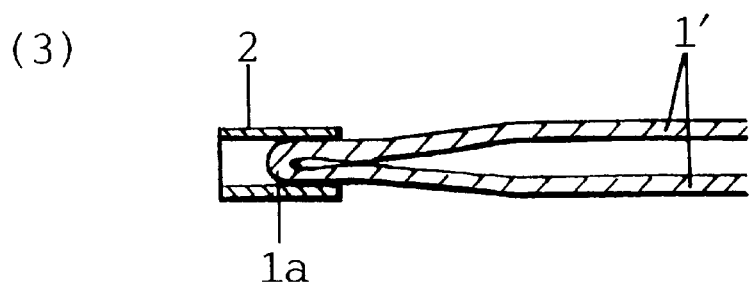
Figure 2:
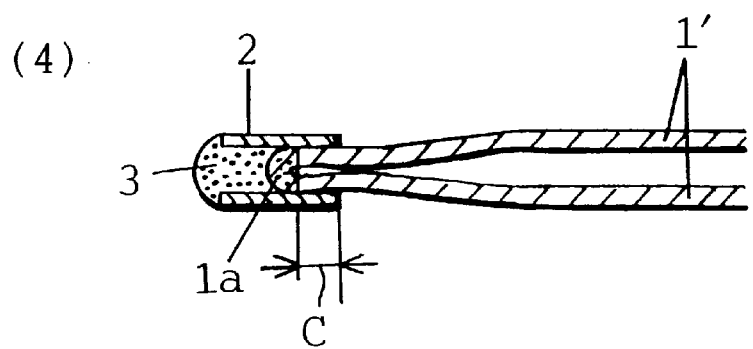

FIG. 2 shows a sequence of steps of processing a distal end bound portion of the elastic wires 1. As shown in part (1) of FIG. 2, a single stock wire 1' is bent in two at the center thereof. Then, two parallel stock wires 1' extending from the bent portion are passed through a distal end binding pipe 2 having an inner diameter sufficient to allow the two stock wires 1' to be loosely fitted therein.

Next, as shown in part (2) of FIG. 2, the stock wires 1' are pulled such that the bent portion 1a enters the distal end binding pipe 2. Consequently, the bent portion 1a of the stock wires 1' is uniformly subjected to force from the bore of the distal end binding pipe 2 that has a circular cross-section and thus smoothly folded.

As shown in part (3) of FIG. 2, the distal end binding pipe 2 is lightly held on the distal end portions of the elastic wires 1 by the expansive restoring force of the distal end bent portion 1a folded in a U-shape. Accordingly, the subsequent fixing operation can be conducted easily.

As shown in part (4) of FIG. 2, the bent portion 1a of the stock wires 1' is secured to the inner surface of the distal end binding pipe 2 by a fixing material 3, e.g. a silver brazing material. Reference character C denotes the range of non-fixed portions of the elastic wires 1. A protuberant portion of the fixing material 3 that projects forward from the distal end binding pipe 2 is rounded smooth by filing.

Referring to FIG. 1, the proximal ends of the pair of elastic wires 1 are bundled together and inserted into a proximal end binding pipe 5 made of stainless steel, for example. In the proximal end binding pipe 5, the bundled proximal ends of the elastic wires 1 are fixed by a fixing material 3, e.g. a silver brazing material, together with a control wire 6 inserted into the proximal end binding pipe 5 from the rear. Thus, the pair of elastic wires 1 are formed into a loop shape as a whole.

It should, however, be noted that in the proximal end binding pipe 5, the elastic wires 1 are not fixed at portions C near the entrance of the binding pipe 5, but fixed by the fixing material 3 at portions thereof which are on the inner side (i.e. rearward) of the non-fixed portions C.

The control wire 6 is axially movably inserted in a flexible sheath 7 over the entire length thereof. The sheath 7 is formed from a tube of tetrafluoroethylene resin, for example. The movement of the control wire 6 is remote-controlled at a control part (not shown) that is connected to the proximal end of the sheath 7.

The proximal end binding pipe 5 has an outer diameter that allows the binding pipe 5 to move back and forth in the sheath 7. In response to an operation of moving the control wire 6 back and forth in the axial direction, the elastic wires 1 come in and out of the distal end of the sheath 7. When withdrawn into the distal end of the sheath 7, the elastic wires 1 are folded. When projecting from the distal end of the sheath 7, the elastic wires 1 expand in the original loop shape by their own elasticity.

To catch a polyp, for example, in the loop formed by the elastic wires 1, the elastic wires 1 are caused to reciprocate axially by moving the control wire 6 back and forth. To pinch tight the polyp caught in the wire loop, the control wire 6 is pulled to withdraw the rear halves of the elastic wires 1 into the distal end of the sheath 7 with the polyp held in the wire loop.

Figure 3:
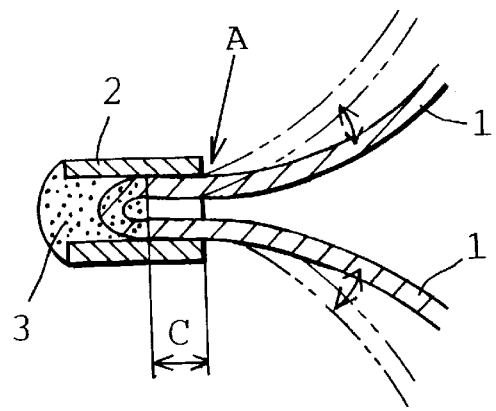
FIG. 3 is a sectional side view showing the distal end bound portion of the first embodiment of the present invention.

During such an operation, as shown in FIG. 3, the distal end portions of the elastic wires 1 are bent with a small radius of curvature at the entrance A of the distal end binding pipe 2 and then unbent.

In this embodiment, however, the elastic wires 1 are not fixed to the distal end binding pipe 2 at the entrance A. At the non-fixed portions C, the elastic wires 1 can freely move in the distal end binding pipe 2. Accordingly, the degree of stress concentration on the elastic wires 1 at the entrance A of the distal end binding pipe 2 is favorably small. Therefore, the elastic wires 1 are unlikely to break or develop undesired bending habits.

The same is true at the proximal end binding pipe 5 where the non-fixed portions C are provided. The degree of stress concentration on the elastic wires 1 at the entrance B of the proximal end binding pipe 5 is also small. Therefore, the elastic wires 1 are unlikely to break or develop undesired bending habits.

Figure 4:
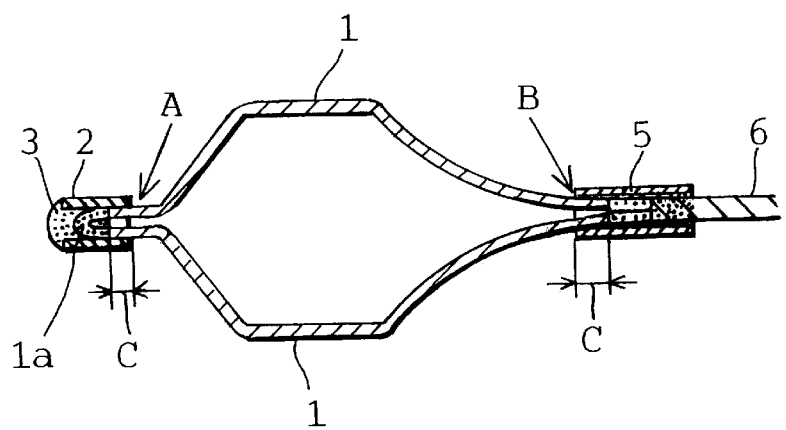
FIG. 4 is a sectional side view showing a distal end portion of a second embodiment of the present invention.

FIG. 4 shows a high-frequency snare for an endoscope according to a second embodiment of the present invention. Elastic wires 1 are bent at a plurality of points in the intermediate portions thereof to form a loop shape as a whole. The other arrangements are the same as in the first embodiment. Illustration of a sheath 7 is omitted.

Figure 5:
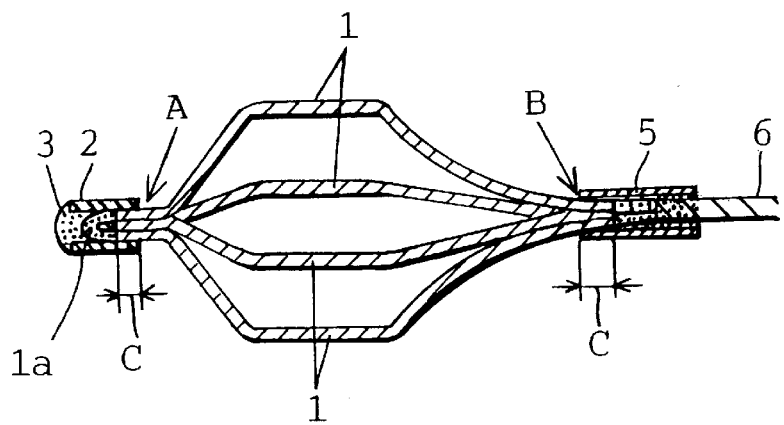
FIG. 5 is a sectional side view showing a distal end portion of a third embodiment of the present invention.

FIG. 5 shows a third embodiment of the present invention. In this embodiment, the present invention is applied to a basket type grasping instrument in which four (two pairs) elastic wires 1 are disposed at intervals of 90 degrees so as to expand in a basket shape. Illustration of a sheath 7 is omitted.

Distal end bent portions 1a of the two pairs of elastic wires 1 are inserted and fixed in a distal end binding pipe 2. Proximal end portions of the four elastic wires 1 are inserted and fixed in a proximal end binding pipe 5. The other arrangements are the same as in the second embodiment.

Figure 6:
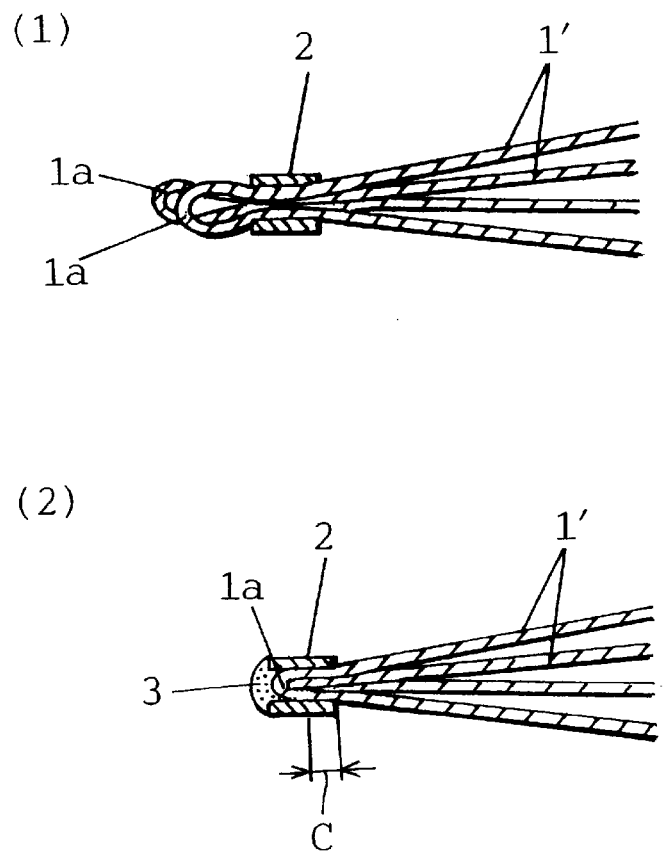
FIG. 6 shows a sequence of steps of processing distal end bound portions of elastic wires in the third embodiment of the present invention.

FIG. 6 shows a sequence of steps of processing distal end bound portions of the elastic wires 1 of the basket type grasping instrument according to the third embodiment. First, as shown in part (1) of FIG. 6, two stock wires 1' are each bent in two at the center thereof. Two pairs of parallel stock wires 1' extending from the bent portions 1a are passed through a distal end binding pipe 2 and then pulled.

Then, as shown in part (2) of FIG. 6, the bent portions 1a of the two stock wires 1' are fixed to the inner surface of the distal end binding pipe 2 by a fixing material, e.g. a silver brazing material or a soldering material. Reference character C denotes the range of non-fixed portions of the stock wires 1'. A protuberant portion of the fixing material 3 that projects forward from the distal end binding pipe 2 is rounded smooth by filing.

Figure 7:
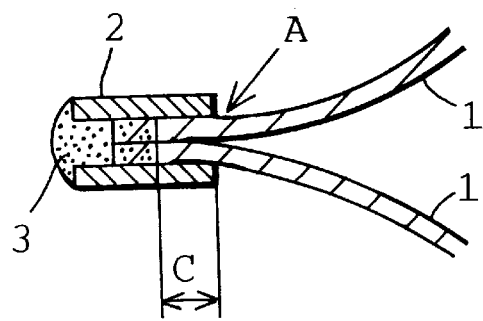
FIG. 7 is a sectional side view showing distal end bound portions of elastic wires in a fourth embodiment of the present invention.

It should be noted that the present invention is not necessarily limited to the above-described embodiments. For example, instead of bending a single stock wire to form a distal end bound portion of a pair of elastic wires 1, two elastic wires 1 which are originally separate from each other, as shown in FIG. 7, may be used as stock wires and fixed in the distal end binding pipe 2.

Figure 8:
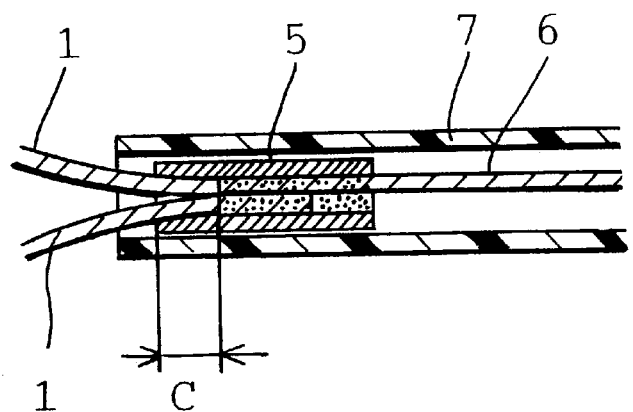
FIG. 8 is a sectional side view showing proximal end bound portions of elastic wires in a fifth embodiment of the present invention.
Figure 9:
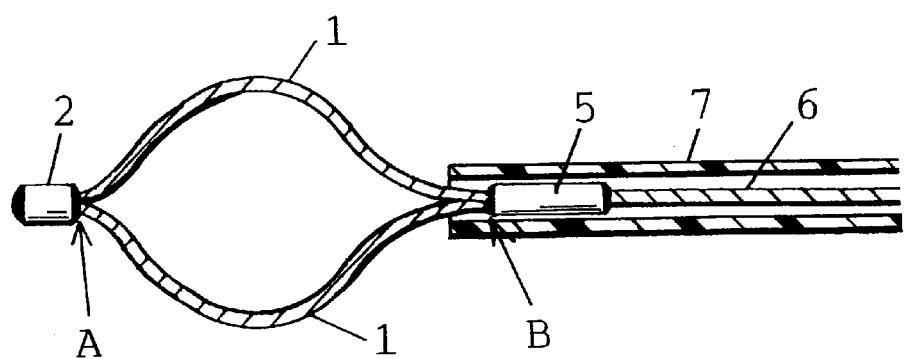
FIG. 9 is a sectional side view showing a distal end portion of a conventional wire loop type instrument for an endoscope.

As shown in FIG. 8, one of a plurality of elastic wires 1 may be further extended rearward from the proximal end binding pipe 5 to use it as a control wire 6.

According to the present invention, a plurality of elastic wires that form a loop are inserted in a bundle into a pipe-shaped member and fixed at portions thereof remote from the entrance of the pipe-shaped member. In other words, portions of the elastic wires in the pipe-shaped member which are near the entrance thereof are not fixed. Therefore, even if an operation of catching a polyp or the like in the wire loop and pinching the caught polyp or the like with the elastic wires is repeated, the elastic wires are unlikely to break or develop undesired bending habits at the bound portions thereof. Thus, the wire loop type instrument according to the present invention exhibits superior durability.

While the invention has been described by reference to specific embodiments chosen for purposes of illustration, it should be apparent that numerous modifications could be made thereto by those skilled in the art without departing from the basic concept and scope of the invention.

We claim:

1. A wire loop type instrument for an endoscope which has a plurality of elastic wires bundled together at distal and proximal ends thereof and adapted to form a loop shape as a whole, said elastic wires being capable of projecting from and withdrawing into a distal end of a sheath, so that when withdrawn into the distal end of said sheath, said elastic wires are folded, and when projecting from the distal end of said sheath, said elastic wires expand in said loop shape by their own elasticity, said wire loop type instrument comprising:

a pipe-shaped member having said elastic wires inserted therein in a bundle at at least one of the distal and proximal ends of said elastic wires; and means for fixing said elastic wires to said pipe-shaped member such that portions of said elastic wires which are in a vicinity of an entrance of said pipe-shaped member are not fixed, but said elastic wires are fixed to said pipe-shaped member at portions thereof which are on an inner side of the vicinity of said entrance.

2. A wire loop type instrument according to claim 1, wherein two of said elastic wires are formed by bending a single stock wire in two at a portion thereof which forms a distal end of said loop shape.

3. A wire loop type instrument according to claim 1, wherein said elastic wires are smoothly curved to form a loop.

4. A wire loop type instrument according to claim 1, wherein said elastic wires are each bent at a plurality of points in an intermediate portion thereof to form a loop.

5. A wire loop type instrument according to claim 1, further comprising:

a control wire for causing said elastic wires to project from and withdraw into the distal end of said sheath, said control wire being axially movably inserted in said sheath, said control wire being fixed at a distal end thereof to a pipe-shaped member having proximal end portions of said elastic wires inserted and fixed therein in a bundle, said distal end of said control wire being inserted into said pipe-shaped member from an opposite side to said elastic wires.

6. A wire loop type instrument according to claim 1, further comprising:

a control wire for causing said elastic wires to project from and withdraw into the distal end of said sheath, said control wire being axially movably inserted in said sheath, said control wire being formed by extending one of said elastic wires at the proximal end thereof.

7. A wire loop type instrument according to claim 1, which is a high-frequency snare for an endoscope in which two elastic wires form a loop.

8. A wire loop type instrument according to claim 1, which is a basket type grasping instrument for an endoscope in which four elastic wires form loops in a basket shape.

* * * * *